(12) United States Patent
Schulz

(10) Patent No.: US 8,942,471 B2
(45) Date of Patent: Jan. 27, 2015

(54) COLOR SEQUENTIAL FLASH FOR DIGITAL IMAGE ACQUISITION

(75) Inventor: Volkmar Schulz, Wuerselen (DE)

(73) Assignee: Koninklijke Philips N.V., Eindhoven (NL)

( * ) Notice: Subject to any disclaimer, the term of this patent is extended or adjusted under 35 U.S.C. 154(b) by 1611 days.

(21) Appl. No.: 12/518,901

(22) PCT Filed: Dec. 13, 2007

(86) PCT No.: PCT/IB2007/055081
§ 371 (c)(1),
(2), (4) Date: Jun. 12, 2009

(87) PCT Pub. No.: WO2008/075266
PCT Pub. Date: Jun. 26, 2008

(65) Prior Publication Data
US 2010/0021038 A1    Jan. 28, 2010

(30) Foreign Application Priority Data

Dec. 19, 2006 (EP) .................................. 06126470

(51) Int. Cl.
*G06K 9/00* (2006.01)
*C12M 1/42* (2006.01)
*H04N 1/60* (2006.01)

(52) U.S. Cl.
CPC *C12M 35/02* (2013.01); *H04N 1/60* (2013.01)
USPC ........................................................ 382/162

(58) Field of Classification Search
None
See application file for complete search history.

(56) References Cited

U.S. PATENT DOCUMENTS

| | | | | | |
|---|---|---|---|---|---|
| 5,754,229 | A | * | 5/1998 | Elabd ............................ | 348/319 |
| 6,373,568 | B1 | | 4/2002 | Miller et al. | |
| 7,364,306 | B2 | * | 4/2008 | Margulis ........................ | 353/31 |
| 8,237,831 | B2 | * | 8/2012 | Adams et al. ................. | 348/277 |
| 8,401,231 | B2 | * | 3/2013 | Maxik et al. .................. | 382/103 |
| 2002/0076219 | A1 | | 6/2002 | Uchino | |
| 2003/0169347 | A1 | * | 9/2003 | Jenkins ...................... | 348/222.1 |
| 2004/0047491 | A1 | * | 3/2004 | Rydbeck ...................... | 382/103 |
| 2004/0061850 | A1 | * | 4/2004 | Fisch et al. ................. | 356/237.2 |
| 2005/0218236 | A1 | * | 10/2005 | Silverbrook et al. ......... | 235/494 |
| 2005/0234302 | A1 | | 10/2005 | MacKinnon et al. | |
| 2006/0067668 | A1 | | 3/2006 | Kita | |
| 2007/0035707 | A1 | * | 2/2007 | Margulis ....................... | 353/122 |
| 2010/0302418 | A1 | * | 12/2010 | Adams et al. ................. | 348/281 |
| 2010/0309350 | A1 | * | 12/2010 | Adams et al. ................. | 348/280 |
| 2011/0050984 | A1 | * | 3/2011 | Schulz .......................... | 348/370 |

FOREIGN PATENT DOCUMENTS

| | | |
|---|---|---|
| EP | 1098190 A2 | 5/2001 |
| WO | 2006101736 A1 | 9/2006 |

* cited by examiner

*Primary Examiner* — Tahmina Ansari
(74) *Attorney, Agent, or Firm* — Yuliya Mathis

(57) ABSTRACT

A method and a System to obtain a more realistic image of an object by acquiring a plurality of e.g. monochromatic images without increasing the structure of a, for example, charged coupled device array by a sequential acquisition of the images by using a color sequential flash.

17 Claims, 7 Drawing Sheets

COLOR SEQUENTIAL FLASH FOR DIGITAL IMAGE ACQUISITION

The present invention relates to a system and method for a digital image acquisition by using a colour sequential flash, and in particular to a system and method for digital image acquisition by using a colour sequential flash having a plurality of different sequential colours.

For a high precise image acquisition it is, on the one hand, required to have a lot of pixels, e.g. one million pixels (1 mega pixel) or higher. On the other hand, a true colour image acquisition requires at least three (red, green, blue) filters, or as indicated by some manufacturers four (red, green, blue, emerald) filters on the pixels, which results in extra cost of the charged coupled device (CCD) chip. Going to a higher resolution requires smaller pixels, which lead to longer exposure time or larger chips, which is a challenge for the production of these filters. Presently, digital cameras are available with eight or more mega-pixel, wherein one of the major problems is to reduce the size of the pixel array allowing a minimisation of the size of the whole device.

In the acquisition of a digital image, the difference of the real world and the picture is mainly due to mismatch of the spectral response of the pixels and the spectral response of the human eye. In most cases, digital cameras operate in a 3RGB—(red, green, blue) colour space, that could not be transformed into the CIE standard colour spaces, e.g. XYZ or sRGB, without introducing additional errors. CIE is the abbreviation of the International Commission on Illumination (Commission Internationale de l'Eclairage).

From US 2004/0061850 A1 an illumination and image acquisition system is known, wherein an inspection illuminates a generally specular surface on an electrical circuit with flashes of light, wherein the flashed light comes from at least two spectrally different sources, and is temporally spaced. A camera forms an optical image of the circuit for each flash of light. Optical images are combined to provide a combined image. For this purpose, US 2004/0061850 A1 provides a red, green and blue illuminator for illuminating the specular surface.

Further, from EP 1 098 190 A2 an illumination and image acquisition system is known, which includes a plurality of colour flash lights operative to illuminate an article to be inspected, and at least one black-and-white camera operative to acquire an optical image of the articles as illuminated by colour flash lights. EP 1 098 190 A2 provides three colour flash lights in red, green and blue.

It would be desirable to provide a system and a method allowing an improved imaging of an object.

The present invention provides a system for providing an improved imaging of an object, wherein the system comprises a plurality of light sources adapted for illuminating the object, wherein at least a part of the light sources are adapted to emit a light having wavelengths of a different range of wavelengths, a controlling unit adapted for controlling the plurality of light sources so that the plurality of light sources illuminate the object in a subsequent number of illumination periods, wherein at least two of the subsequent illumination periods the object is illuminated by wavelengths of a different range of wavelengths, an acquiring unit adapted for acquiring at least four sets of image data of the object in at least two illumination periods, and a reconstruction unit adapted for reconstructing the at least four acquired sets of image data to an image of an at least four dimensional colour space.

The inventive system allows for an improved imaging of an object due to the acquisition of at least four sets of image data allowing to provide an image of at least four dimensional colour space, which reproduces the imaged object more realistically in view of the spectral response of the human eye. Due to a sequential acquisition, the acquiring unit may be kept small due to a low number of pixels. Owing to the system comprising at least four light sources adapted to emit light having wavelengths of a different range of wavelengths, the spectral response of the human eye can be reproduced more exactly. As a matter of fact, also more than four light sources may be used, in particular a plurality of light sources, each having a different range of wavelengths. The higher the number of different wavelengths, the higher the dimension of the resulting colour space.

It should be noted that different ranges of wavelengths means that the ranges are not identical, but may overlap. Further, a range does not have to be continuous, but may also have an interruption, so that a range may also be a composition of partial ranges. A range may also be one or a plurality of monochrome wavelengths. Subsequent illumination periods mean illumination periods of a sequence, which may also have interruptions. The illumination periods may also be consecutive, i.e. without interruptions in between, or may have overlap.

The mode, that one light source illuminates the object in a period also includes the mode that a plurality of light sources illuminate the object in that period, but the one light source illuminates with an increased intensity over the remaining ones in that period. This means that the reconstruction unit is also adapted to determine the overlap, and is capable of eliminating the overlap, so that the system can also be used with a daylight illumination.

According to an exemplary embodiment of the present invention, the acquiring unit of the system is a monochrome acquisition device. Thus, the system uses, for example, a monochrome charged coupled device (CCD) array for an image acquisition with a colour-sequential flash. The flash may have several coloured high power light emitting diodes (LED) that were rapidly flashed time-sequentially. According to one exemplary embodiment, only one colour is flashing in one period. In such a single period, one image is taken via the CCD array.

This procedure will lead to a series of images each illustrating an object which is illuminated with a different colour, respectively. This sequence is used to reconstruct the spectral reflectivity of the object. Using more than three colours, in particular much more than three colours (ten or more) leads to a spectral like image of the object. Thus, a precise spectral reconstruction of the reflectivity of the imaged object per pixel is possible. Thus, for example, the colour temperature of the virtual illumination can be changed after the image acquisition process. Some of the main advantages are a spectral like image acquisition, a simple adoption to a target colour space, a cheap and easy non-filtered CCD or photo diode array, a smaller CCD chip, a simple calibration of the flash and not of the filters of the CCD, a very sharp image due to the use of motion correction and low exposure times, a possibility to work in different colour spaces, and a tunable illumination colour after an image acquisition.

In particular, additional costs of, for example, red, green and blue filters can be saved, as well as the requirement for true sRGB filters. Further, a transformation in the wrong colour space can be avoided, as well as a high exposure time of the CCD. Also the resolution of the CCD can be reduced by the factor of three or four due to the filters.

According to a further exemplary embodiment of the present invention, the light sources of the system are adapted to emit wavelengths of at least two of the different ranges of wavelengths, wherein at least one of the ranges includes at least two different sub ranges of wavelengths, and the acquiring unit is adapted to acquire at least two sets of image data of the object in each of at least one illumination periods, and the acquiring unit is sensitive to at least one of the different sub-ranges of wavelengths for each of at least two sets of image data. The sub range constitutes a part of one of the different ranges. It should be noted that the sub-ranges also may overlap partially or totally. The sub-ranges do not have to be identical to each other. The light sources thus emit, for example, two different wavelengths in, for example, two illumination periods, wherein the acquiring unit is capable of sensing for example two images, each corresponding to each of the two different wavelengths, so that in the present example in each illumination period two sets of image data can be acquired. Consequently, after two illumination periods, four sets of image data are acquired, wherein each of the sets of image data represents a different spectral response of the object. Thus, a plurality of images can be acquired at the same time with a colour flash having a spectrum comprising a plurality of colours, so that the combination of a multi-colour acquisition and a sequential acquisition resulting in different images leads to an optimisation with respect to the size of the acquisition device and the number of subsequent illumination periods having a different colour spectrum.

According to a further exemplary embodiment of the present invention, the plurality of light sources are arranged such that the illumination is carried out in a substantially equal angle of incidence for the corresponding wavelengths of the different range of wavelengths. Thus, the plurality of obtained images substantially do not differ in the locations of light and shadowed areas of the object.

According to a further exemplary embodiment, the acquiring unit is a multi-colour acquisition device, which allows to acquire a plurality of sets of image data at the same time.

According to a further exemplary embodiment, the light sources and the acquisition device are adapted to obtain a reconstructed set of image data of a CIE standard colour space. The CIE standard colour space more precisely represents the spectrum of the human eye. Thus, it is possible to obtain true colour images, and to avoid a mismatch of the spectral response of the pixels and the spectral response of the human eye.

According to a further exemplary embodiment, the plurality of light sources cover a wavelength emitting spectrum of 380 nm to 830 nm. Thus, the complete visual spectrum of the human eye is covered. It should be noted that the present invention may also be applied to infrared light and ultraviolet light, and further to any other range of electro-magnetic radiation, where it is appropriate.

According to a further exemplary embodiment, the light sources each comprise one or more light emitting diodes (LED), wherein the light emitting diodes are adapted to emit light having a wavelength of one or more predetermined ranges of wavelength.

It should be noted that a light source may comprise only one light emitting diode, but may also comprise a plurality of LEDs of the same colour, as well as a plurality of LEDs of different colours, i.e. of a plurality of different ranges of wavelength.

According to a further exemplary embodiment, the light sources each comprise one or more laser diodes, wherein the laser diodes are adapted to emit light having a wavelength of one or more predetermined ranges of wavelength.

It should be noted that a light source may comprise only one laser diode, but may also comprise a plurality of laser diodes of the same colour, as well as a plurality of laser diodes of different colours, i.e. of a plurality of different ranges of wavelength.

According to a further exemplary embodiment, the acquisition device is a charged coupled device (CCD).

According to a further exemplary embodiment, the method for providing an improved imaging of an object comprises illuminating the object with a plurality of light sources in a subsequent number of illumination periods, wherein at least a part of the light sources emit light having wavelengths of a different range of wavelengths, and wherein in at least one of the subsequent illumination period, the object is illuminated by wavelengths of a different range of wavelengths, acquiring at least four sets of image data of the object in at least two illumination periods, and reconstructing at least four acquired sets of image data to a set of image data of an at least four dimensional colour space.

According to a further exemplary embodiment of the present invention, the method further comprises illuminating the object in at least four of the subsequent illumination periods with light sources being adapted to emit light having wavelengths of a different range of wavelengths in each of at least four illumination periods, and acquiring a set of image data of the object in each of at least four illumination periods.

According to a further exemplary embodiment, each of the light sources illuminate the object in one of a subsequent number of illumination periods.

According to a further exemplary embodiment, the acquiring is carried out as a monochrome acquiring.

According to a further exemplary embodiment, at least one of the different ranges of wavelengths include at least two different sub ranges of wavelengths, and the method further comprises acquiring at least two sets of image data of the object in each of the at least one illumination period, wherein the acquiring of each of at least two sets of image data is sensitive to at least one of the different sub ranges of wavelengths.

According to a further exemplary embodiment, at least two sets of image data are acquired parallel in time in each of the at least one illumination periods.

According to a further exemplary embodiment, the illumination periods of the plurality of light sources are consecutive and/or repeat periodically. Thus, the method also provides for the capability of imaging a moved object, i.e. to obtain a movie.

According to a further exemplary embodiment, the illumination is carried out in a substantially equal angle of incidence for each of the wavelengths of the different range of wavelengths.

According to a further exemplary embodiment, the acquiring is carried out as a multi-colour acquiring.

According to a further exemplary embodiment, there is provided a programme element, which, when being executed by a processor, is adapted to carry out the method described above.

According to a further exemplary embodiment, there is provided a computer readable medium having stored thereon the above programme element.

It should be noted that the description above applies for a system, as well as the method, the programme element and the corresponding computer readable medium.

It may be seen as the gist of the present invention to obtain a plurality of e.g. monochromatic images without increasing the structure of a, for example, charged coupled device array by a sequential acquisition of the images by using a colour sequential flash.

These and other aspects of the present invention will become apparent from and elucidated with reference to the embodiments described hereinafter.

Exemplary embodiments of the present invention will be described in the following with reference to the following drawings.

A DETAILED DESCRIPTION OF THE EXEMPLARY EMBODIMENTS

Figure 1:
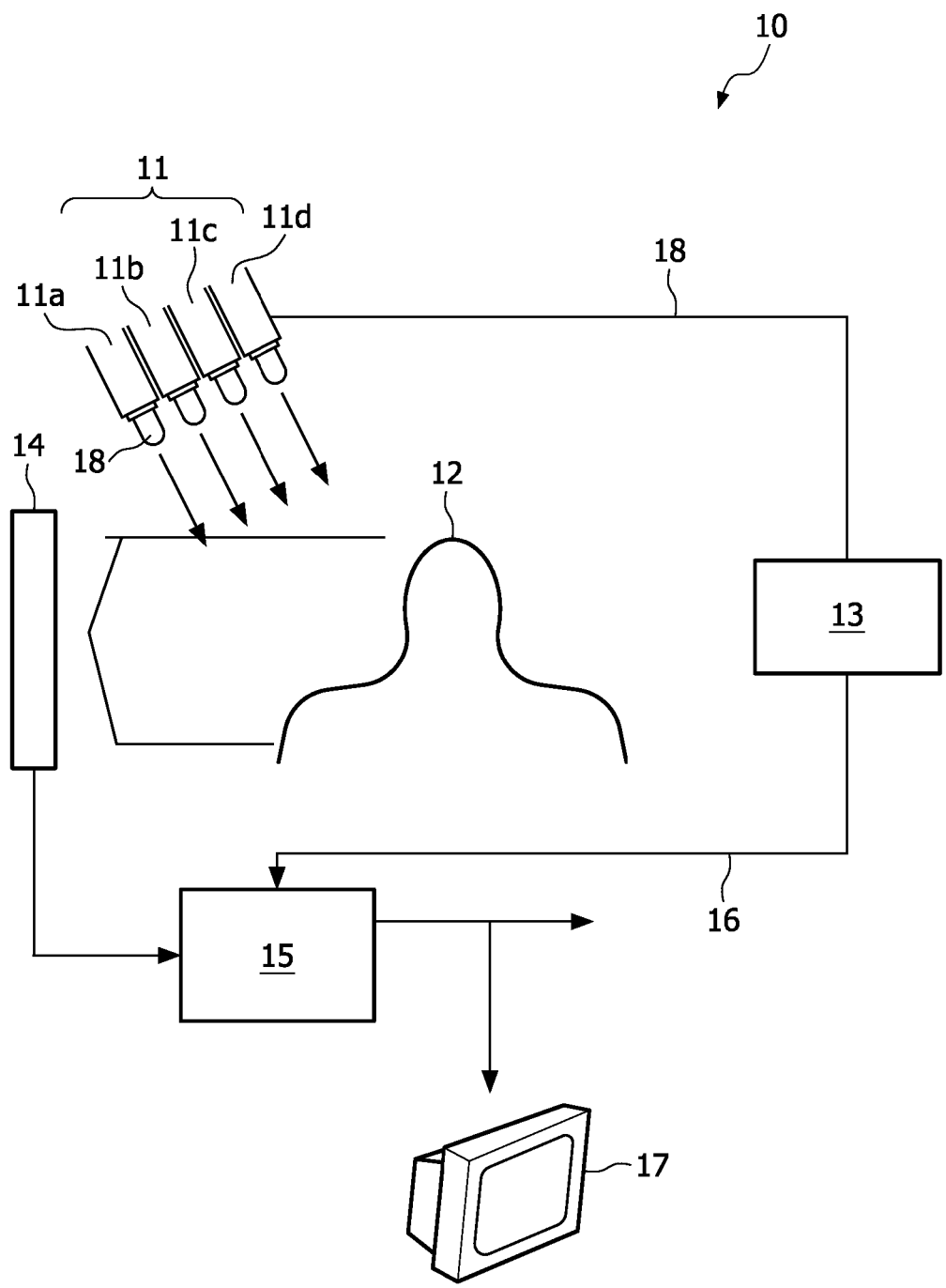
FIG. 1 shows a schematic diagram of the system according to an exemplary embodiment of the present invention.

An object 12 is illuminated by a light source 11 or a plurality of light sources 11a, 11b, 11c, 11d. The light sources may be provided with light emitting diodes (LEDs), for example, high power LEDs. The LEDs may be rapidly flashed time sequentially, so that only one colour is flashing in a period. Thus, the object 12 may be illuminated by a single colour in each period, so that the object appears, in a subsequent order, in different colours. An acquiring unit 14 receives the reflected light from the object 12 and comprises, for example, a CCD chip. It should be noted that also any other kind of device may be used for receiving and acquiring light reflected from the object 12, like a photo diode array etc. The acquiring unit 14 may include a mono-colour or multi-colour acquisition device. A multi-colour acquisition device is necessary when illuminating the object 12, for example, by two light sources 11, 11a-11d at the same time, so that the acquisition device may obtain two images of two different colours, i.e. the acquisition device is sensitive to two different wavelengths.

The acquiring unit 14 acquires sets of image data and may provide the data to a reconstruction unit 15, which is adapted for reconstructing the acquired sets of image data 21a-21d to a set of image data 22 of a multi-dimensional colour space. The reconstruction unit may output the reconstructed set of image data to a display device 17 or may output the data to a further device for any post-processing (not shown). The plurality of light sources 11, 11a-11d may be controlled by a controlling unit 13, wherein the line 18 between the controlling unit 13 and the light sources 11, 11a-11d is adapted to transmit a controlling signal for a plurality of light sources. This may be achieved, for example, by a line having a plurality of separated wires or by a line being capable of carrying a controlling signal having a plurality of channels (wire or wireless). The controlling unit 13 may also be connected to the reconstruction unit 15 by means of a line 16, for example, by a line having a plurality of separated wires or by a line being capable of carrying a controlling signal having a plurality of channels (wire or wireless), in order to synchronise the controlling of the light sources 11, 11a-11d with the received sets of image data 21a-21d received from the acquiring unit 14. Thus, the sets of image data 21a-21d may be allocated to the correct corresponding wavelength emitted by the light sources 11, 11a-11d.

According to an exemplary embodiment of the present invention, the number of light sources 11 is at least four, however, the present invention is not limited thereto. It is also possible to provide only two light sources, wherein each of the light sources include, for example, an LED 18 capable of emitting light of two different wavelengths, wherein such an LED may also be seen as two light sources. Further, there may be also provided a large number of light sources covering a wide range of the visible light with respect to the human eye, for example, substantially 380 nm to 830 nm. Substantially means at least 450-700 nm.

According to a further exemplary embodiment, the light sources, 11, 11a-11d are provided close to each other such that the angle of incidence with respect to the object 12 to be illuminated is substantially the same so that the different images do not substantially differ with respect to the light and dark locations due to shadows occurring during lateral illumination.

Figure 2:
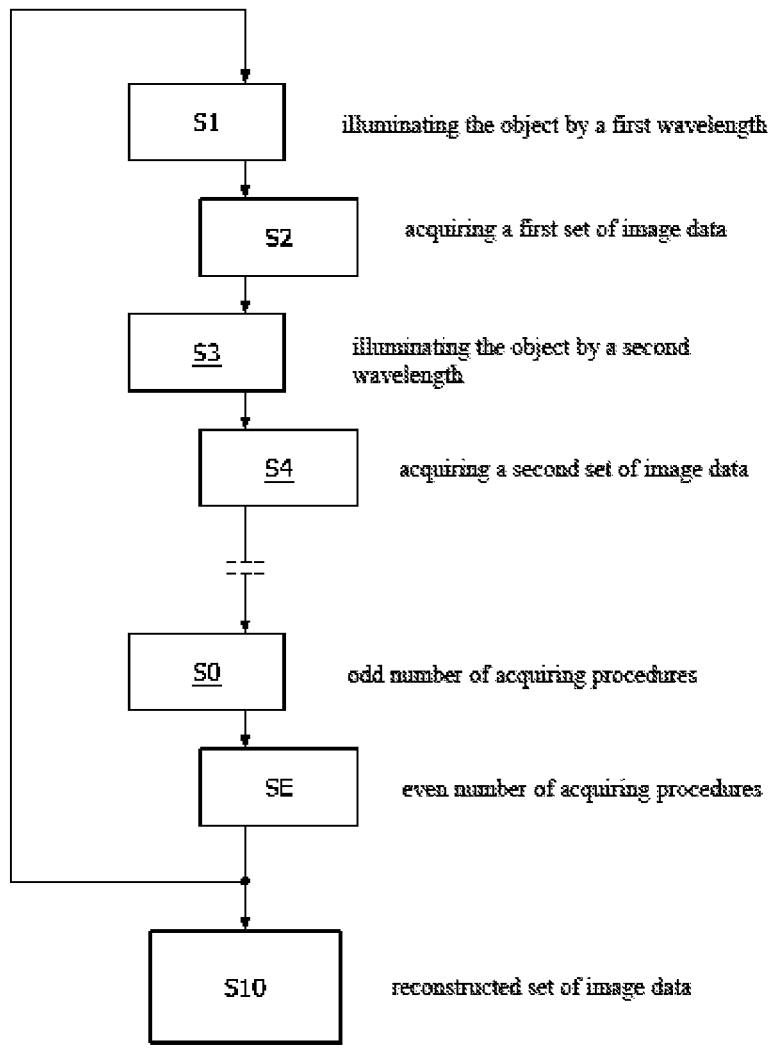
FIG. 2 shows a flow chart of a method according to an exemplary embodiment of the present invention.

FIG. 2 shows a flow chart according to an exemplary embodiment of the present invention.

In a subsequent order, an object 12 is illuminated S1 by, for example, a light having a predetermined wavelength. Then, a set of image data is acquired S2. Subsequently, the object is illuminated by a light having a second predetermined wavelength being different from the first predetermined wavelength S3 and the set of image data is acquired S4 with respect to the second illumination procedure S3. The illumination and acquiring procedure can be repeated as often as desired, depending on the different colours of the plurality of light sources, i.e. the number of different ranges of wavelengths. SO represents the odd numbered procedure of illuminating and SE represents the even numbered procedure of acquiring. The procedure of the steps S1-SE can be periodically repeated, e.g. for obtaining a movie. At the same time, a set comprising the plurality of sets of image data may be provided to the reconstruction unit so that the plurality of acquired sets of image data 21a-21d may be reconstructed S10 to obtain a set of image data 22 of a multi-dimensional colour space. A dimension of the colour space depends on the number of different wavelengths illuminating the object 12 in a subsequent order.

Figure 3:
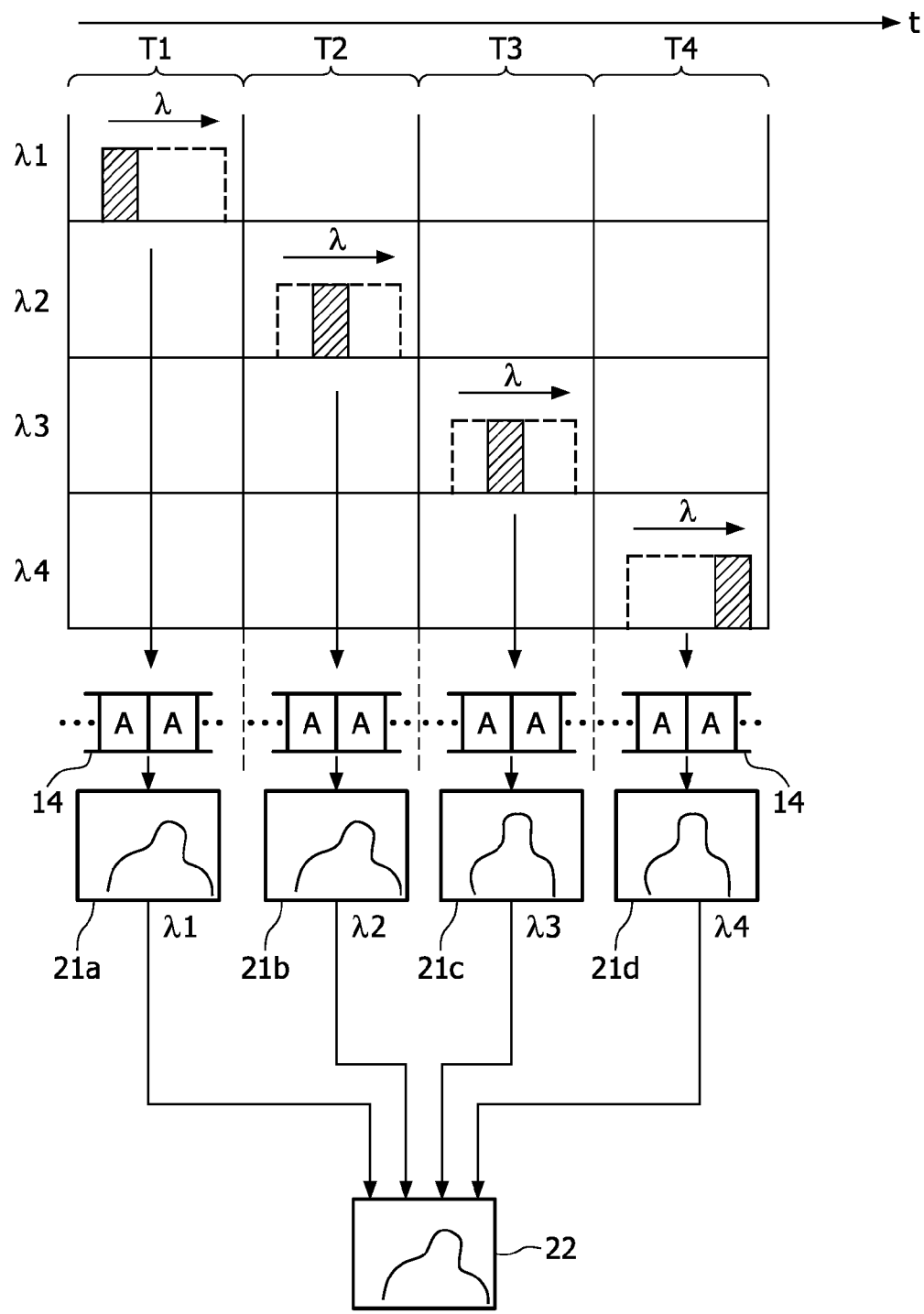
FIG. 3 shows a detailed schematic procedure of the method of an exemplary embodiment of the present invention as shown in FIG. 2.

FIG. 3 gives a detailed impression of an exemplary embodiment of the present invention.

In a first illumination period T1 the object 12 is illuminated by a light having a wavelength $\lambda 1$. It should be noted that wavelength may be a dominant wavelength, but may also include a range of wavelengths and is not limited to a monochromatic wavelength. The object 12 reflects the radiation of the illuminated light having the wavelength $\lambda 1$ so that the reflected radiation may be detected by an acquiring unit 14. The A represents a single pixel capable of registering the intensity of the reflected light. The pixels A may be pixels of, for example, a CCD chip. The CCD chip provides a set of image data 21a including the image data corresponding to the wavelength $\lambda 1$.

In a subsequent illumination period T2 the object 12 is illuminated by a second wavelength $\lambda 2$, wherein the acquisition device or the CCD chip receives the reflected light of the wavelength $\lambda 2$ and provides a set of image data 21b corresponding to the intensity received by the CCD chip with respect to the wavelength $\lambda 2$. The procedure will be repeated during the illumination periods T3 with a light having the wavelength of λ3, and during an illumination period T4 with a light having the wavelength λ4. Thus, in the present example, four sets of image data 21a-21d are provided, each corresponding to one of the light sources each having different wavelengths λ1 to λ4. The four sets of image data 21a-21d are fed to the reconstruction unit, which reconstructs the four sets of image data 21a-21d to a reconstructed set of image data 22. It should be noted that any optical arrangement (not shown) may be provided for focussing etc.

Figure 4:
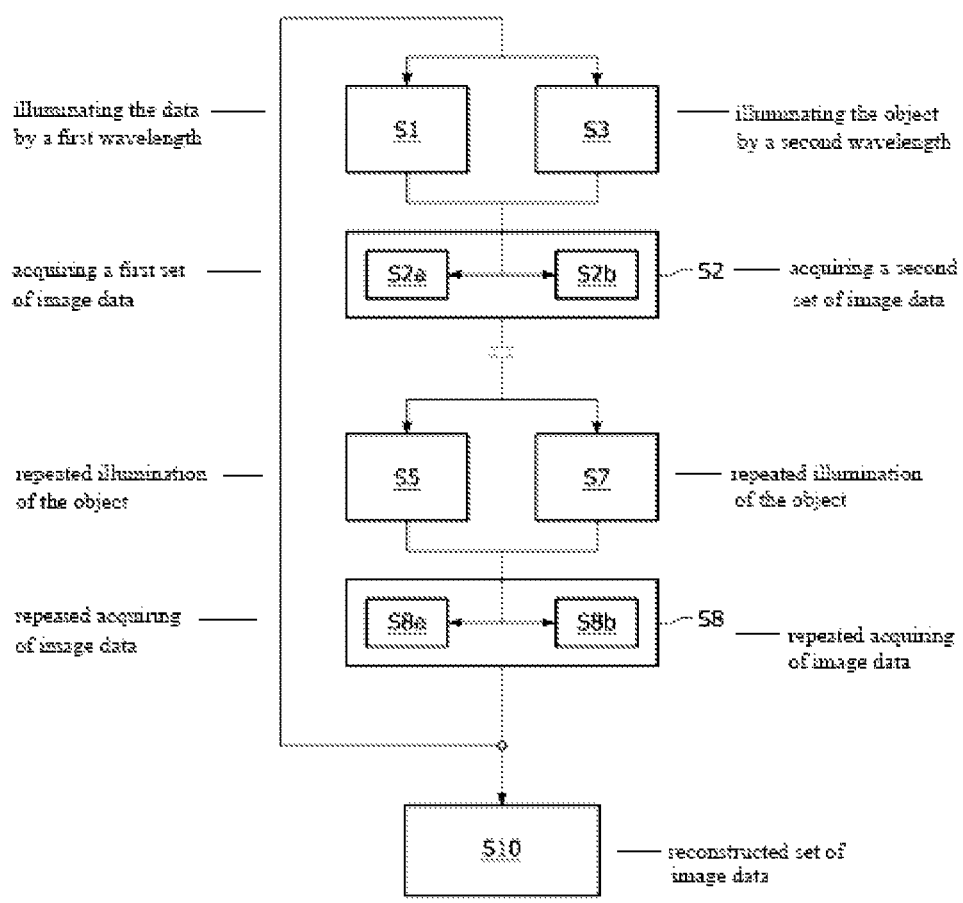
FIG. 4 shows a flow chart of a method according to another exemplary embodiment of the present invention.

FIG. 4 shows a schematic flow of a method according to another exemplary embodiment of the present invention.

According to the exemplary embodiment illustrated by FIG. 4, the illumination S1, S3 of the object 12 is carried out in a first illumination period T5 with two different wavelengths λ1, λ3. Thus, the object 12 is illuminated S1 by light of a first wavelength and at the same time illuminated S3 by light of a second wavelength or a wavelength range being different to the first wavelength. Then, sets of image data are acquired S2, S2a, S2b for each of the light of a particular wavelength, so that during the acquiring procedure two sets of image data are obtained, one corresponding to the illumination S1 with a light of the first wavelength λ1, and the other corresponding to the illumination S3 by light of the second wavelength λ3. This procedure can be repeated as often as required, which is correspondingly illustrated by S5, S7, S8, S8a, S8b. The number of repetitions depends on the number of required image data sets.

The complete procedure S1 to S8 can be repeated, wherein the plurality of images are fed to the reconstruction unit for reconstructing S10 the obtained and acquired images, to a set of image data of a multi-dimensional colour space. In the exemplary embodiments shown in FIG. 4, the object 12 is illuminated four times, S1, S3, S5, S7, wherein two illuminations S1, S3 and S5, S7 are carried out at the same time. Thus, in each of the illumination periods two sets of image data are acquired S2a, S2b and S8a, S8b, so that in total four sets of image data are available for reconstructing S10 a set of image data of a four dimensional colour space.

By repeating the procedure, a plurality of multi-dimensional colour space images can be obtained, which is useful, for example, when producing a movie.

Figure 5:
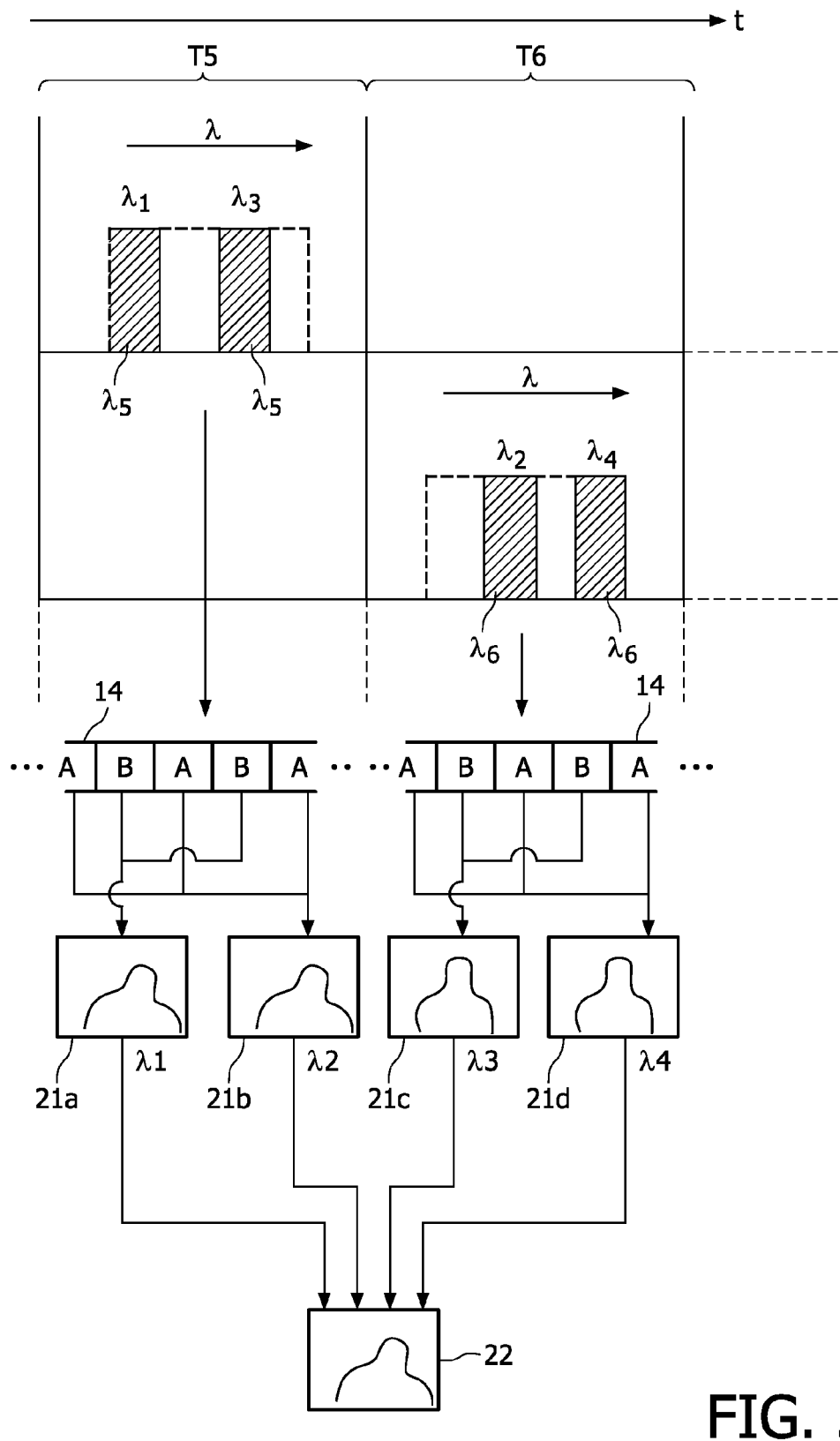
FIG. 5 shows a detailed schematic procedure of the method according to the further exemplary embodiment of the present invention as shown in FIG. 4.

FIG. 5 gives a schematic detailed illustration of the procedure according to the exemplary embodiment illustrated with respect to FIG. 4.

In a first illumination period T5 the object 12 is illuminated by a light having a first range λ5 of wavelengths, which constitutes the sub ranges λ1, λ3. Thus, the object 12 may be illuminated by two different sub ranges of a wavelength λ1, λ3 at the same time. In a subsequent illumination period T6 the object is illuminated by light of a different range of wavelengths λ6, which is different from the range of wavelengths λ5 of the previous illumination period T5. The range of wavelengths λ6 includes the sub ranges λ2, λ4, so that the object during the illumination period T6 is illuminated by the wavelengths λ2 and λ4. In this example, the wavelengths λ1 to λ4 are selected such that the resulting image data sets lead to a four dimensional colour space. As a matter of fact, the present invention is not limited to only four wavelengths.

The reflected light is detected and acquired by the acquiring unit comprising an acquisition device like a CCD chip. The acquisition device comprises, in the present example, two different kinds of pixels A, B, wherein pixels A are, for example, sensitive to the wavelengths λ1 and λ2, wherein the pixels B are sensitive to the wavelengths λ3 and λ4. During a first illumination period T5 the object is illuminated by light of the wavelengths λ1 and λ3, so that the pixels A (sensitive to λ1 and λ2) may detect the light of the wavelength λ1, and the pixels B (sensitive to λ3 and λ4) may detect the light of the wavelength λ3. In the subsequent illumination period T6 the pixels A (sensitive to λ1 and λ2) may detect light of wavelength λ2, and the pixels B (sensitive to λ3 and λ4) may detect light of the wavelength λ4. Thus, the pixels A are used in the first illumination period T5 for acquiring image data of an image corresponding to the wavelength λ1, wherein in a subsequent illumination period T6 the same pixels are used for acquiring image data corresponding to the wavelength λ2. Correspondingly, pixels B acquire image data corresponding to λ3 in the illumination period T5 and image data corresponding to wavelength λ4 in the illumination period T6. Thus, in the illumination period T5 two sets of image data 21a, 21c corresponding to the wavelengths λ1 and λ3, respectively, may be obtained, and in the illumination period T6 two sets of image data 21b, 21d may be obtained corresponding to the wavelengths λ2 and λ4, respectively. Thus, during only two illumination periods T5, T6 in total four images corresponding to four different wavelengths or wavelength ranges can be obtained to achieve a set of image data 22, of a four-dimensional colour space.

It should be noted, that FIG. 5 is only an exemplary illustration, and that during one illumination period also more than two different wavelengths can be applied for the illumination, and also an acquisition device can be applied being capable of distinguishing more than two different light wavelengths, so that the maximum number of images may be determined by multiplying the number of different subsequent illumination periods with the number of different images, which can be distinguished by the acquisition device 14.

Figure 6:
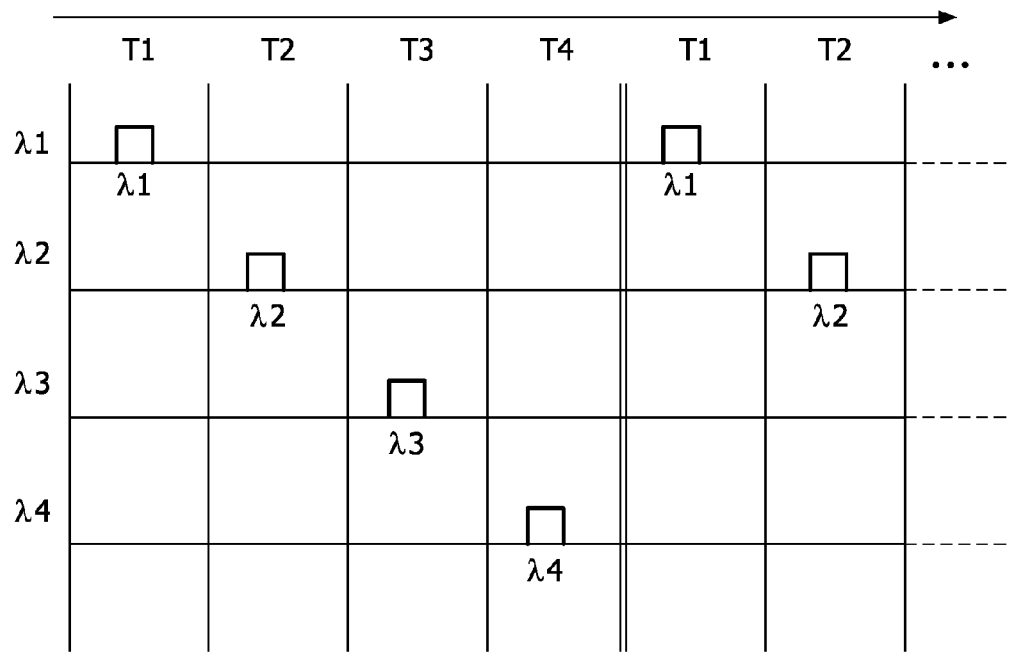
FIG. 6 shows a schematic overview of the sequence of colour flashes according to an exemplary embodiment of the present invention.

FIG. 6 illustrates the sequence of illumination periods, wherein the sequence of λ1, λ2, λ3 and λ4 is periodically repeated, since the illumination periods T1, T2, T3, T4 are periodically repeated. It should be noted, that the present invention is not limited to the allocation of T1 to the wavelength λ1, the illumination period T2 to the wavelength λ2 and so on, as is illustrated in FIG. 6. It should also be noted that according to an exemplary embodiment, the illumination periods are consecutive in the sequence, however, the present invention is not limited thereto. Moreover, the sequence may also have interruptions or intermediate periods between the illumination periods. Further, each of the periods may have the same lengths or may be of a different length.

Further, the present invention is not limited to four illumination periods and further, is not limited to four different wavelengths.

To obtain a better result, the provision of more wavelengths is advantageous.

Figure 7:
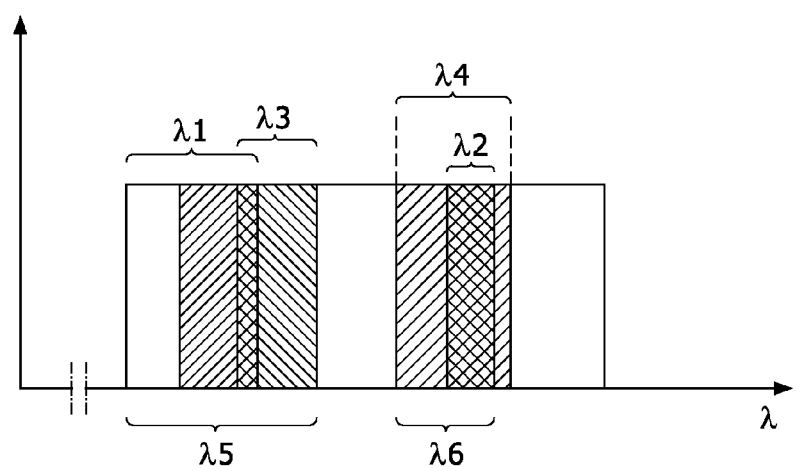
FIG. 7 shows a spectrum of different ranges of wavelengths according to exemplary embodiments of the present invention.

FIG. 7 illustrates a spectrum of light, which can be recognised by the human eye. In particular, this spectrum bay be in the range from 380 nm to 830 nm. In FIG. 7, the spectrum is illustrated as a rectangular, however, the real spectrum does not have steep slopes and is not uniform over the range of the spectrum. However, this illustration is advantageous for the illustration.

FIG. 7 shows two different ranges of wavelengths λ5, λ6, wherein each of the different ranges comprises two sub ranges λ1, λ3 and λ2, λ4. For the range λ5, the sub ranges overlap partially. The range λ6 comprises two sub ranges λ2, λ4, wherein the range λ2 is totally overlapped by the range λ4. It should be noted that the combination of the ranges λ5 and λ6 may also constitute a range comprising sub ranges λ5 and λ6, wherein the sub ranges λ5 and λ6 in this case do not overlap, and do not constitute in total a continuous range.

When using overlapping ranges in any kind, it is necessary to distinguish the portions of the sets of image data corresponding to the different wavelengths or different ranges of wavelengths λ1, λ3, or λ2, λ4. This may be proceeded by a differential image acquisition, which allows the use of these techniques also during daylight.

The differential image acquisition can be expressed by $$wij(dl) = gnij(dl) + bnij(dl) + mij(dl)$$

$$b\_wij = w(dl) + bij(f)$$

$$r\_wij = w(dl) + rij(f)$$

$$g\_wij = w(dl) + gij(f)$$

Here, wij (dl) is the pixel-signal given via the daylight illumination, which contains all superimposed colors. b_wij is pixel signal given by the illumination via daylight and the flash, here color blue. Thus, the interested pixel signal b1 could be calculated from the subtraction:

$$bij(f) = b\_wij - wij((dl)).$$

An approximation of a signal of the pixel $S_{ij}$ is given via the following equation.

$$S_{ij} = \int_{\lambda=380nm}^{\lambda=830nm} p(\lambda) r(\lambda) \bar{x}(\lambda) s_{ij}(\lambda) d\lambda \approx \int_{\lambda=380nm}^{\lambda=830nm} p(\lambda) r(\lambda) x(\lambda) s_{ij}(\lambda) d\lambda$$

In this equation $p(\lambda)$ is the power spectrum that illuminates the surface of the object, $r(\lambda)$ is the unknown reflectivity of this object, $x(\lambda)$ is the color matching function and $s_{ij}(\lambda)$ is the spectral response of the CCD pixel ij. Thus, in conventional image acquisition on main task is to precisely approximate the color matching functions x, y, and z.

Instead of using these special filters on top of the CCD pixel $S_{ij}$, we will reconstruct the reflectivity of the illuminated object. Thus we assume the reflectivity being a linear combination of a set of basis functions $b_n(\lambda)$.

$$r(\lambda) \approx \sum_{n=1}^{N} \phi_n b_n(\lambda)$$

For that, the projection into a color space via the color matching function is not required anymore. At a given time $t_k$ where the object is illuminated with the light given via the flash $p_k$ this equation could be rewritten to:

$$S_{ij}(t_k) \approx \sum_{n=1}^{N} \phi_n \int_{\lambda=380nm}^{\lambda=830nm} P_k(\lambda,) b_n(\lambda) s_{ij}(\lambda) d\lambda = \sum_{n=1}^{N} \phi_n \gamma_{nk}$$

Repeating this acquisition with the other N−1 colors leads to a system of N equations that determines the unknown coefficients $\Phi_n$ and thus the reflectivity of the object w.r.t. the applied model. It should be noted that all items being integrated are known and thus the integral is known.

$$\begin{bmatrix} S_{ij}(t_1) \\ \vdots \\ S_{ij}(t_N) \end{bmatrix} = \begin{bmatrix} \gamma_{11} & \cdots & \gamma_{1N} \\ \vdots & \ddots & \vdots \\ \gamma_{N1} & \cdots & \gamma_{NN} \end{bmatrix} \begin{bmatrix} \phi_1 \\ \vdots \\ \phi_N \end{bmatrix}$$

This procedure has to be applied to all pixels.

Figure 8:
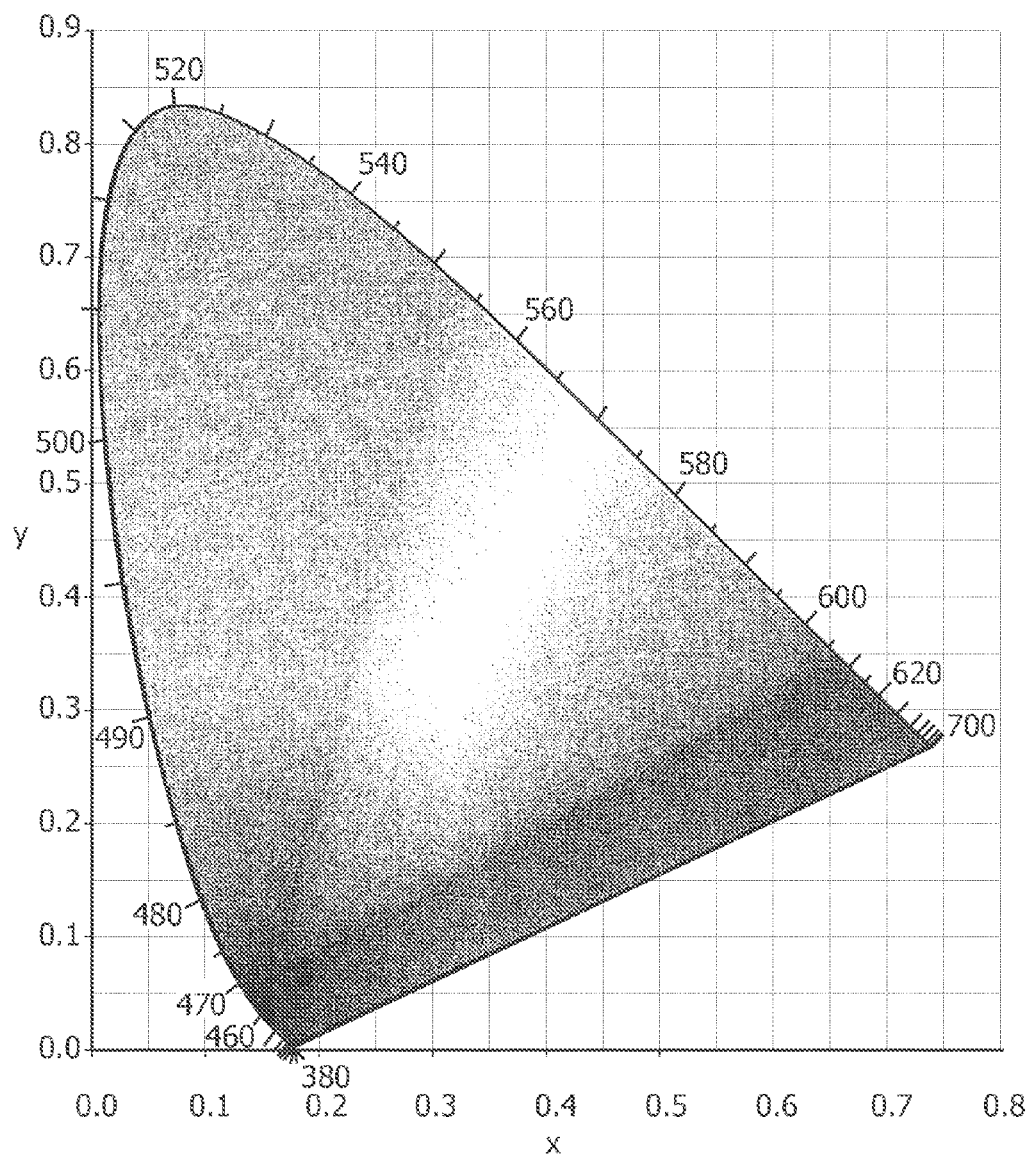
FIG. 8 shows a CIE standard colour space.

FIG. 8 shows a diagram of a CIE colour space as a two-dimensional illustration, wherein the numbers and the parabolic line express the wavelength, and therefore, when illustrating the colour, cover the complete spectrum. The straight line between 380 and 700 is denoted as the purple line. The CIE colour space is used as the standard reference for defining colours, and a reference for other colour spaces.

It should be noted that the present invention may be also applied for light sources emitting infrared light or ultraviolet light and corresponding acquiring units. The invention may also be applied to any other electro-magnetic radiation instead of light.

The invention constitutes an alternative way of image acquisition via a CCD sensor as used in almost all digital cameras or mobile phones. Instead of using complicated filtered RGB or RGBE CCD chips, this invention may use a monochrome CCD array with a sequenced colour flash light in order to acquire true-colour images. The proposed technique is mainly related to image acquisition where the flash light contributes significantly to the acquisition process.

The present invention may be applied in a digital image acquisition and future devices for both pictures and movies. Further, the present invention may be applied in spectral measurements of surfaces, e.g. precise determination of the colour of an object.

It should be noted that the term 'comprising' does not exclude other elements or steps and the 'a' or 'an' does exclude a plurality. Also elements described in association with different embodiments may be combined.

It should be noted that the reference signs in the claims shall not be construed as limiting the scope of the claims.

The invention claimed is:

1. A system for providing an improved imaging of an object, the system comprising: a plurality of light sources adapted for illuminating the object during a plurality of illumination periods, wherein each of the plurality of light sources is adapted to emit light having at least two different wavelengths during the illumination period in which the light source is illuminated; a controlling unit adapted for controlling the plurality of light sources so that different light sources of the plurality of light sources illuminate the object in each of a plurality of subsequent illumination periods, such that the object is illuminated by different wavelengths during each subsequent illumination period, wherein at least a part of the plurality of light sources are arranged such that the illumination is carried out in a substantially equal angle of incidence for the corresponding wavelengths; an acquiring unit adapted for detecting light reflected from the illuminated object and acquiring at least four sets of image data of the object in the plurality of subsequent illumination periods; and a reconstruction unit adapted for combining the at least four acquired sets of image data into a reconstructed set of image data of the object, wherein the reconstructed set of image data of the object comprises an at least four-dimensional color space.

2. The system of claim 1, further comprising at least four light sources adapted to emit light having wavelengths of a different range of wavelengths.

3. The system of claim 2, wherein the acquiring unit is a monochrome acquisition device.

4. The system of claim 1, wherein the light sources are adapted to emit at least two different wavelengths having different ranges, and wherein at least one of the ranges includes at least two different sub-ranges of wavelengths; the acquiring unit is adapted to acquire at least two sets of image data of the object in each of the at least two illumination periods; and the acquiring unit is sensitive to at least one of the different sub-ranges of wavelengths for each of the at least two sets of image data.

5. The system of claim 1, wherein the acquiring unit is a multicolor acquisition device.

6. The system of claim 1, wherein the light sources and the acquiring unit are adapted to obtain the reconstructed set of image data of a CIE standard color space.

7. The system of claim 1, wherein the plurality of light sources cover a wavelength emitting spectrum of substantially 380 nm to 830 nm.

8. The system of claim 1, wherein the light sources comprise one or more light emitting diodes, wherein each of the light emitting diodes are adapted to emit light of a wavelength of one or more different ranges of wavelengths.

9. The system of claim 1, wherein the light sources comprise one or more laser diodes, wherein each of the laser diodes are adapted to emit light of a wavelength of one or more different ranges of wavelengths.

10. The system of claim 1, wherein the acquisition device is a charged coupled device.

11. A method for providing an improved imaging of an object, the method comprising: illuminating the object with a plurality of light sources in a plurality of subsequent illumination periods, wherein each of the plurality of light sources is adapted to emit light having at least two different wavelengths during the illumination period in which the light source is illuminated, and wherein in at least two of the plurality of subsequent illumination periods the object is illuminated by different light sources of the plurality of light sources such that the object is illuminated by different wavelengths during subsequent illumination periods, wherein the illumination is carried out in a substantially equal angle of incidence for each of the different wavelengths; acquiring at least four sets of image data of the object from light reflected from the illuminated object in the plurality of subsequent illumination periods, and reconstructing all of the at least four acquired sets of image data into a reconstructed set of image data of the object, wherein the reconstructed set of image data of the object comprises an at least four-dimensional color space.

12. The method of claim 11, further comprising illuminating the object in at least four of the subsequent illumination periods with light sources adapted to emit light having wavelengths of a different range of wavelengths in each of the at least four illumination periods, and acquiring a set of image data of the object in each of the at least four illumination periods.

13. The method of claim 12, wherein acquiring is carried out as a monochrome acquiring.

14. The method of claim 11, wherein at least two different wavelengths having different ranges include at least two different sub-ranges of wavelengths, and the method further comprises acquiring at least two sets of image data of the object in each of the at least two illumination periods, wherein the acquiring of each of the at least two sets of image data is sensitive to at least one of the different sub-ranges of wavelengths.

15. The method of claim 14, wherein in each of at least one illumination periods the at least two sets of image data are acquired parallel in time.

16. The method of claim 11, wherein the illumination periods of the plurality of light sources are consecutive and/or repeated periodically.

17. The method of claim 11, wherein the acquiring is carried out as a color acquiring.

* * * * *